United States Patent [19]

Merger et al.

[11] Patent Number: 4,596,678
[45] Date of Patent: Jun. 24, 1986

[54] MULTIPLE-STEP PROCESS FOR THE PREPARATION OF HEXAMETHYLENE DIISOCYANATE-1,6 AND/OR ISOMERIC ALIPHATIC DIISOCYANATES WITH SIX CARBON ATOMS IN THE ALKYLENE RESIDUE

[75] Inventors: Franz Merger, Frankenthal; Friedrich Towae, Ludwigshafen; Hans Hellbach, Lampertheim; Gunther Isbarn, Ludwigshafen; Waldemar Koehler, Frankenthal, all of Fed. Rep. of Germany

[73] Assignee: BASF Aktiengesellschaft, Ludwigshafen, Fed. Rep. of Germany

[21] Appl. No.: 600,143

[22] Filed: Apr. 13, 1984

[30] Foreign Application Priority Data

Apr. 23, 1983 [DE] Fed. Rep. of Germany ....... 3314788

[51] Int. Cl.$^4$ ............................................. C07C 69/00
[52] U.S. Cl. ............................................. 560/344 CM
[58] Field of Search .................... 260/453 PC, 453 AL

[56] References Cited

FOREIGN PATENT DOCUMENTS 0028338  5/1981  European Pat. Off. .

OTHER PUBLICATIONS

Wagner & Zook, Synthetic Org. Chem., (1965), p. 647.

Sandler Org. Functional Group Prep., vol. 2-II, (1971), p. 244.

*Primary Examiner*—Alan Siegel
*Attorney, Agent, or Firm*—William G. Conger; Joseph D. Michaels

[57] ABSTRACT

Hexamethylene diisocyanate and/or isomeric alkylene diisocyanates having 6 carbon atoms in the alkylene radical, preferably 2-methylpentamethylene 1,5-diisocyanate and/or 2-ethyltetramethylene 1,4-diisocyanate are prepared without the use of phosgene in a multiple-step process by means of (a) reacting hexamethylene 1,6-diamine and/or isomeric alkylene diamines having 6 carbon atoms in the alkylene radical with urea and alcohol in the presence of dialkyl carbonate and/or carbamic acid alkyl ester as well as, in some cases, catalysts to form hexamethylene 1,6-dialkylurethane and/or isomeric alkylene dialkylurethanes having 6 carbon atoms in the alkylene radical, (b) separation and return to reaction step (a) of alcohol, dialkyl carbonate, and/or carbamic acid alkyl ester from the reaction mixture (c) evaporation of the hexamethylene 1,6-dialkylurethane and/or isomeric alkylene dialkylurethanes having 6 carbon atoms in the alkylene radical, (d) cleavage of the vaporized diurethanes into hexamethylene diisocyanate and/or isomeric alkylene diisocyanate having 6 carbon atoms in the alkylene radical and alcohol, and (e) fractional condensation of the cleavage products.

11 Claims, No Drawings

MULTIPLE-STEP PROCESS FOR THE PREPARATION OF HEXAMETHYLENE DIISOCYANATE-1,6 AND/OR ISOMERIC ALIPHATIC DIISOCYANATES WITH SIX CARBON ATOMS IN THE ALKYLENE RESIDUE

BACKGROUND OF THE INVENTION

1. Field of the Invention

This invention deals with isocyanate synthesis. More specifically, it discloses a non-phosgene process for the preparation of hexamethylene diisocyanate and isomeric diisocyanate.

2. Description of the Prior Art

The commercial production of hexamethylene 1,6-diisocyanate is based on the phosgenation of hexamethylenediamine to form hexamethylene bis(carbamyl chloride) and its thermal cleavage into hexamethylene diisocyanate and hydrogen chloride. Aside from serious environmental and safety problems involved with the use of phosgene, this process also has further disadvantages. For example, the production of hexamethylene diisocyanate results in rather poor volume-time yields. In addition to hexamethylene diisocyanate, several by-products result, of which the most important, 6-chlorohexyl isocyanate, has the further disadvantage that a relatively elaborate procedure is required to separate it from the hexamethylene diisocyanate.

A problem with this process lies in the high conversion of chlorine via phosgene and carbamyl chloride in hydrogen chloride, the toxicity of phosgene, as well as the corrosiveness of the reaction mixture and the low stability of the solvents that are generally used. There have been numerous attempts to prepare isocyanates, preferably aromatic di- and/or polyisocyanates, without using phosgene.

In EP-A 28 338 aromatic di- and/or polyisocyanates are prepared in a two-step process, whereby primary aromatic di- and/or polyamines are reacted in the first step with O-alkylcarbamic acid esters in the presence or absence of catalysts and, in some cases, urea and alcohol to form aryldi- and/or polyurethanes, and the ammonia formed in this process may, in some cases, be separated off, and the aryldi- and/or polyurethanes that were obtained can be converted into aromatic di- and/or polyisocyanates in the second reaction step by means of thermal cleavage. In this way, aromatic di- and/or polyisocyanates can be prepared with high yields and without using phosgene.

DE OS No. 31 08 990 describes the preparation of isophorone diisocyanate through the thermal cleavage under pressure of 3-ethoxycarbonylaminomethyl-3,5,5-trimethyl-1-ethoxycarbonylaminocyclohexane in the presence of dibenzyltoluene as a solvent and a catalyst mixture of toluene methylsulfonate and diphenyl tin dichloride. No information is given on obtaining the initial components, isolating and purifying the initial components, possible recovery of the solvent, or on the catalyst mixture. Thus, calculations of the economic feasibility of the process cannot be made.

Based on the information in German Patent Application Nos. P 32 27 748.2, P 32 48 018.0 and P 31 42 627.1 hexamethylene dialkyl urethanes can be decomposed without using catalysts or in a fluidized bed containing carbon into hexamethylene diisocyanate and alcohols. However, this process cannot be used to obtain hexamethylene diisocyanate yields greater than 90 percent, since the cleavage products partially recombine. The yield can be further decreased by the subsequent purification distillation that is needed for the hexamethylene diisocyanate.

SUMMARY OF THE INVENTION

The object of the invention at hand was to prepare hexamethylene diisocyanate and/or isomeric alkylene diisocyanates having 6 carbon atoms in the alkylene radical, all subsequently abbreviated as HDI, with high selectivity in high volume-time yields, economically, and in a simple manner without using expensive or hazardous starting materials or auxiliaries.

This objective was met by reacting hexamethylene diamine and/or isomeric aliphatic diamines having 6 carbon atoms in the alkylene radical, all subsequently abbreviated as HDA, in hexamethylene dialkyl diurethanes and/or isomeric alylene dialkyl diurethanes having 6 carbon atoms in the alkylene radical, all subsequently abbreviated as HDU, and their thermal cleavage into HDI and alcohols.

Hence, the subject of the invention is a multiple-step process for the preparation of HDI characterized by
(a) reacting HDA with urea and alcohol in the presence of dialkyl carbonates and/or alkyl carbamates as well as, in some cases, catalysts to form HDU, whereby the resulting ammonia is simultaneously separated off,
(b) separating the alcohol, the dialkyl carbonates, and/or alkyl carbamates from the resulting reaction mixture and, preferably, returning them to reaction step (a),
(c) evaporating the HDU in an evaporator at temperatures from 200° to 300° C. and a pressure from 0.1 to 200 mbar,
(d) thermally cleaving the vaporized diurethane into HDI and alcohol at temperature in excess of 300° C. and a pressure from 0.1 to 200 mbar in a pyrolysis reactor, and
(e) fractionally condensing the cleavage products.

In one of the preferred embodiments of the process, the resulting reaction mixture (b) is fractionated in two steps whereby
(i) the alcohol is distilled off in the first step until a residual alcohol concentration of from 1 to 30 weight percent based on the total weight of the residual mixture is obtained and said distilled alcohol is returned to reaction step (a), and
(ii) in the second step, the remaining alcohol, the dialkykl carbonate, and/or the alkyl carbamate is separated from the HDU and, in some cases, the oligourea polyurethanes by means of stripping with inert gas and the distillate is returned to reaction step (a).

DESCRIPTION OF THE PREFERRED EMBODIMENTS

In the process of the invention, HDI can be prepared industrially with very good yields and without producing any problems. Particularly advantageous with the multiple-step process is the fact that the initially used and intermediately formed dialkyl carbonates and/or alkyl esters of carbamic acid, and the alcohol can be returned to reaction step (a) and reused without the need for additional expensive purification and recovery processes. The presence of dialkyl carbonates and/or alkyl carbamates also results in high HDU selectivities. The process is well suitable for a continuous operation.

Among the iomeric aliphatic isocyanates with six carbon atoms in the alkylene radical are, in particular, 2-methylpentamethylene-1,5-diisocyanate and 2-ethyl-tetramethylene-1,4-diisocyanate. The process of the invention is thus preferably used to prepare the two isomers cited above and, in particular, hexamethylene diisocyanate as well as mixtures of these diisocyanates.

In a purely formal sense, the overall process of the invention can be represented by the following equation:

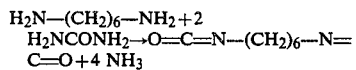

$H_2N—(CH_2)_6—NH_2 + 2 H_2NCONH_2 \rightarrow O=C=N—(CH_2)_6—N=C=O + 4 NH_3$

To prepare the HDU in reaction step (a), HDA is reacted with urea and alcohol in a molar ratio of from 1.8 to 2.5 moles urea and 2 to 10 moles alcohol, preferably from 2.0 to 2.3 moles urea and 3 to 6 moles alcohol per mole of HDA in the presence or absence of catalysts at reaction temperatures from 160° to 300° C., preferably from 180° to 250° C., and more preferably from 185° to 240° C., and at a pressure which, depending on the alcohol used, lies between 0.1 and 60 bar, preferably between 1 and 40 bar. Under these reaction conditions, reaction times of from 0.5 to 50 hours, preferably from 3 to 15 hours result.

In principle, all aliphatic alcohols are suitable as the alcohols. Preferably, however, those alcohols will be selected whose boiling points are sufficiently far from the boiling point of the HDI obtained through thermal cleavage, so that, on the one hand, the most quantatative possible separation of the cleavage products HDI and alcohol is possible and, on the other hand, so that the resulting HDUs, in some cases in addition to the oligourea polyurethanes, can be evaporated with as little decomposition as possible.

For these reasons, alcohols such as methanol, ethanol, n-propanol, n-butanol, iso-butanol, n-pentanol, iso-pentanol, n-hexanol, or mixtures of said alcohols and, in particular, n-propanol, n- and/or iso-butanol are preferably used.

As already discussed, the reaction in reaction step (a) is performed in the presence of dialkylcarbonates in amounts from 1 to 30 mole percent, preferably from 5 to 25 mole percent, or alkyl esters of carbamic acid in amounts from 1 to 20 mole percent, preferably from 5 to 18 mole percent, based on the HDA. However, it is preferable to use mixtures of dialkyl carbonates and alkyl esters of carbamic acids in the cited quantitative ratios. Preferably, those dialkyl carbonates and/or esters of carbamic acid are used whose alkyl radicals correspond to the alkyl radical of the alcohol being used.

In order to increase the rate of reaction, the HDUs are prepared in the presence of catalysts. Such catalysts are suitably used in amounts from 0.1 to 20 weight percent, preferably from 0.5 to 10 weight percent, and more preferably from 1 to 5 weight percent, based on the weight of the HDA. Inorganic or organic compounds are suitable as the catalysts, provided that they contain one or more, preferably one cation, of the metals of groups IA, IB, IIA, IIB, IIIA, IIIB, IVA, IVB, VA, VB, VIB, VIIB and VIIIB of the periodic system defined in accordance with the *Handbook of Chemistry and Physics,* 14th Edition, published by the Chemical Rubber Publishing Co., 23 Superior Ave. N.E., Cleveland, Ohio, preferably halogenides such as chlorides and bromides, sulfates, phosphates, nitrates, borates, alcoholates, phenylates, sulfonates, oxides, oxide hydrates, hydroxides, carboxylates, chelates, carbonates, and thio- or dithiocarbamates. Typical examples are the cations of the following metals: lithium, sodium, potassium, magnesium, calcium, aluminum, gallium, tin, lead, bismuth, antimony, copper, silver, gold, zinc, mercury, cerium, titanium, vanadium, chromium, molybdenum, manganese, iron, cobalt, and nickel. Preferably, cations of lithium, calcium, aluminum, tin, bismuth, antimony, copper, zinc, titanium, vanadium, chromium, molybdenum, managanese, iron, and cobalt are used. The catalysts can also be used in the form of their hydrates or ammoniates without clearly noticeable disadvantages.

The following compounds are examples of typical catalysts: lithium methanolate, lithium ethanolate, lithium propanolate, lithium butanolate, sodium methanolate, potassium tert-butanolate, magnesium methanolate, calcium methanolate, tin(II)chloride, tin(IV)chloride, lead acetate, lead phosphate, antimony(III)chloride, antimony(V)chloride, aluminum isobutylate, aluminum trichloride, bismuth(III)chloride, copper(II)acetate, copper(II)sulfate, copper(II)nitrate, bis(triphenylphosphinoxide) copper(II)chloride, copper molybdate, silver acetate, gold acetate, zinc oxide, zinc chloride, zinc acetate, zinc acetonylacetate, zinc octoate, zinc oxalate, zinc hexylate, zinc benzoate, zinc undecylenate, cerium(IV)oxide, uranyl acetate, titanium tetrabutanolate, titanium tetrachloride, titanium tetraphenolate, titanium naphthenate, vanadium(III)chloride, vanadium acetonylacetate, chromium(III)chloride, molybdenum(-VI)oxide, molybdenum acetylacetonate, tungsten(-VI)oxide, manganese(II)chloride, manganese(II)acetate, manganese(III)acetate, iron(II)acetate, iron(III)acetate, iron phosphate, iron oxylate, iron(III)chloride, iron(III)bromide, cobalt acetate, cobalt chloride, cobalt sulfate, cobalt naphthenate, nickel chloride, nickel acetate, and nickel naphthenate, as well as mixtures of the above.

It has been found to be advantageous to separate the resulting ammonia immediately from the reaction mixture, for example by means of distillation. The apparatus used for this, for example a distillation column, is operated at temperatures from 60° to 150° C., preferably from 65° to 120° C., so that the column does not become coated with ammonium carbamate, which is formed in very small amounts from ammonia and carbon dioxide through the decomposition of urea.

After the reaction is completed, the alcohol, the dialkyl carbonates, and/or other alkyl esters of carbamic acid are separated from the resulting reaction mixture (b) and are held in readiness for reutilization in subsequent batches; with a continuous process, however, they are preferably returned directly to reaction step (a).

As explained above, the separation of the cited compounds is preferably performed in two steps. In the first step the alcohol is distilled off until a residual alcohol content of from 1 to 30 weight percent is obtained, preferably from 2 to 15 weight percent, based on the weight of residual reaction mixture, and said alcohol is returned to reaction step (a).

The more concentrated reaction mixture, which for the most part is comprised of HDU and, in some cases, oligourea polyurethanes, as well as the remaining alcohol, dialkyl carbonate, and/or alkyl ester of carbamic acid, is further concentrated in a second step in a stripping column with from 50 to 5000 liters, preferably from 100 to 1000 liters, inert gas per liter of the concentrated reaction mixture from the first concentrating step per hour at stripping temperatures from 50° to 200° C., preferably from 120° to 180° C., in order to almost completely separate the remaining alcohol, the dialkyl carbonates, and/or the alkyl esters of carbamic acid. Suitable inert gases which may be used for this process are, for example, nitrogen, carbon monoxide, rare gases, and methane. The stripped, low-boiling point compounds are condensed, in some cases stored for an interim period, and reserved for use in further batches. With the continuous process, they are returned directly to reaction step (a).

The residue obtained after stripping (b), which is primarily comprised of HDU and, in some cases, oligourea polyurethanes, can be evaporated as a liquid, a solid, as a melt suspension or in a solvent which is inert under the reaction conditions, said evaporation being performed in an evaporator, and said volatilized HDU can then be thermally cleaved in a subsequent cleaving reactor (d).

In the preferred embodiment of the process of the invention, the residue (b) is charged into the evaporator in a solution-free condition in the form of a melt heated to from 80° to 180° C., preferably from 100° to 150° C., by means of a metering pump.

Evaporators which have proven to be particularly effective at temperatures from 200° to 300° C., preferably from 220° to 300° C., and more preferably from 240° to 280° C., and at a pressure from 0.1 to 200 mbar, preferably from 5 to 100 mbar, are film evaporators or fluidized bed evaporators. However, any other evaporators can be used, for example, screw evaporators, A.P. reactors (manufacturer: Krauss-Maffei), metal coil or agitated bed evaporators.

When film evaporators are used, it is indeed possible to evaporate the entire amount of HDU charged to the evaporator by using a sufficient amount of heat. However, it is advantageous to discharge part of the charged HDU, together with any oligourea polyurethane that may be present, in an unevaporated form as a melt, since this achieves a significant cleaning effect on the evaporator wall. The weight ratio of evaporated to unevaporated HDU can be varied over wide ranges, for example from 20:80 to 90:10. The melt discharged from the evaporator is preferably returned directly to reaction step (a), the diurethanation step.

The HDU vapors (c) are charged into the cleaving reactor and are thermally cleaved therein at a temperature in excess of 300°, preferably from 310° to 480° C. and more preferably from 310° to 440° C., and at a reduced pressure, for example, from 0.1 to 200 mbar, preferably from 0.1 to 100 mbar and more preferably from 1 to 50 mbar, in a discontinuous or, preferably, continuous process in HDI and alcohol.

The cleaving reactor, which generally is of a column-like shape, can have a cross section of any desired shape. Preferably, long, cylinderical cleaving reactors are used. The ratio of the inside diameter to the length of the cleaving reactor is generally from 1:2 to 1:1000, preferably from 1:10 to 1:500. The cleaving reactors can be positioned vertically or horizontally or at positions between vertical and horizontal. Preferably, tubular ovens are used as the cleaving reactors, said tubular ovens having inside tube diameters of approximately 10 to 100 mm and tube lengths of approximately 0.5 to 5 m.

It is desirable to perform the cleavage operation in the presence of thermally stable reactor packing. Suitable packing material includes all temperature-resistant and gas permeable materials such as beads, wool, rings, and/or chips of coal, steel, brass, copper, zinc, aluminum, titanium, chromium, cobalt, nickel and/or quartz. Some of these materials, such as steel, brass, aluminum, and zinc, have proven to be particularly effective and are, therefore, used preferentially, since they produce better cleavage results. Here, it has not yet been determined whether catalytic or physical effects are involved, for example, better heat transfer, or whether a synergistic combination of both effects is involved.

From the cleaving reactor, the dissociation products found in the vapor phase, which consists almost exclusively of HDI and alcohol, are directed into a two-step vapor condensation device (e). In the first condensation step, which is operated dependent on the system pressure of from 0.1 to 100 mbar at temperatures from 60° to 120° C., the HDI condenses out almost completely.

When using the preferred hexamethylene 1,6-dibutylurethane at a system pressure from 20 to 40 mbar it is desirable to maintain a condensation temperature of from 70° to 100° C. In the second condensation step, primarily alcohol is condensed. This alcohol is returned to reaction step (a). The temperature of the second condensation step is based on the boiling point of the alcohol which is to be condensed. In the cleavage of hexamethylene 1,6-dibutylurethane, it is desirable at the above system pressure to maintain a condensation temperature of from 5° to 30° C. The HDI obtained in the first condensation step is generally subjected to a purification distillation and thereafter is greater than 98 weight percent pure, preferably over 99 weight percent. The bottom product resulting from this purification distillation is also returned to reaction step (a).

Depending on the condensation temperatures which are selected and the system pressure which is used, varying amounts of alcohol can be also condensed in the first condensation step and varying amounts of HDI can also be condensed in the second condensation step. In a preferred embodiment, the HDI that is also condensed in the second condensation step is allowed to react with excess alcohol to form HDU, and after being separated from the alcohol, this is again returned to the evaporation and cleavage steps. However, in another preferred embodiment it is also possible to return the HDU together with the dialkyl carbonate and/or alkyl esters of carbamic acid to reaction step (a) once the alcohol has been separated off.

In a similar manner, the alcohol of the preferred embodiment that has also condensed in the first condensation step can be allowed to react with excess HDI, and the product mixture can be returned to the evaporation and cleaving steps after distillative separation of the HDI, or, preferably can be mixed with the alcohol contained in the second condensation step and returned to reaction step (a).

The HDI prepared in accordance with the process of the invention is extremely suitable for the preparation of polyurethane or polyurethane-polyurea plastics and, in particular, for light-resistant polyurethane paints and coatings.

The invention is described in more specific detail in the following non-limiting examples. In these examples, unless otherwise specified, all parts refer to parts by weight.

EXAMPLE 1

In the first vessel in a three-step mixing vessel cascade with an attached column and pressure control valve, in which a mixture mainly comprised of hexamethylene dibutyl urethane and n-butanol in addition to hexamethylene oligourea polyurethanes, dibutyl carbonate, and carbamic acid butyl ester, 1.044 parts urea, 1.015 parts hexamethylenediamine, and 0.1029 parts n-butanol were added and heated to from 215° to 220° C., whereby a pressure developed which stabilized at from 6 to 8 bar. The resulting ammonia was separated in the attached column operated at from 80° to 85° C. with almost complete reflux of the n-butanol from the reaction solution. The reaction discharge from the third vessel in the mixing vessel cascade was released into a packed column operating at standard pressure. Approximately 3.2 parts/hour n-butanol was obtained in addition to residual ammonia at the head outlet of this column. This head discharge was returned directly to the first vessel in the mixing vessel cascade. The distillation bottoms were charged into a stripping column operated at 165° C. About 250 volumes per hour per volume reaction mixture of nitrogen was blown through this column as a stripping gas. The 0.98 part/hr. mixture of residual butanol, dibutyl carbonate, and carbamic acid butyl ester was obtained at the top of the stripping column. The stripping column bottoms were discharged into a thin-film evaporator evacuated to 33 mbar and heated to 260° to 270° C., which was operated in such a way that the ratio of evaporated hexamethylene 1,6-dibutyl urethane to the disharging melt was approximately 9:1. The discharging melt was mixed with the head products of the stripping column and was returned to the second vessel in the mixing vessel cascade. The urethane vapors were metered into a cleavage reactor having ca. 3 liters empty volume. This reactor was packed with V2A wire mesh rings of ca. 3 mm diameter. The temperature in the cleavage reactor averaged 410° C. The cleavage gases emerging from this reactor were fractionally condensed in a subsequent two-step condensation device. In the first condenser, operated at 85° C., a mixture of 94.6 weight percent hexamethylene diisocyanate and 5.4 weight percent hexamethylene monobutylurethane monoisocyanate was collected. From this, a subsequent distillation produced 1.395 parts/hour hexamethylene diisocyanate having a purity greater than 99 percent (selectivity based on charged hexamethylene diamine: 95.7 percent). The bottoms from the purification distillation were mixed with the discharge obtained from the second condenser operated at from 10° to 12° C.; this mixture was heated to from 100° to 110° C., and was charged back into the third vessel in the mixing vessel cascade.

EXAMPLE 2

The same procedure as used in Example 1 was followed, however, 2-methylpentamethylene 1,5-dibutylurethane was used in the mixing vessel cascade instead of hexamethylene dibutylurethane. In doing this, 660 parts 2-methylpentamethylene-1,5-diamine, 680 parts urea, and 76 parts n-butanol were added during the course of one hour. In this case, about 2400 parts/hour n-butanol was obtained at the top of the first distillation column and was cycled back into the cascade. At the top of the stripping column, 1430 parts of a mixture comprising dibutyl carbonate, carbamic acid butyl ester, and residual butanol was obtained. This mixture was returned to the second vessel in the mixing vessel cascade together with the evaporator discharge. The evaporator was run in such a way that the ratio of evaporated 2-methylpentamethylene-1,5-dibutylurethane to discharging melt was approximately 46:54. A mixture of ca. 74 weight percent 2-methylpentamethylene 1,5-diisocyanate and 26 weight percent methylpentamethylene monourethane monoisocyanates condensed in the first condenser. From this condensate, 887 parts/hour 2-methylpentamethylene 1,5-diisocyanate was obtained in a subsequent distillation process at a purity ≧98 percent (selectivity based on charged 2-methylpentamethylene 1,5-diamine: 93.6 percent).

The embodiments of the invention in which an exclusive privilege or property is claimed are defined as follows:

1. A multiple-step process for the preparation of hexamethylene diisocyanate-1,6 and/or isomeric aliphatic diisocyanates with 6 carbon atoms in the alkylene residue wherein
   (a) hexamethylenediamine-1,6 and/or isomeric alkylenediamines with 6 carbon atoms in the alkylene residue are reacted with urea and alcohol in the presence of dialkyl carbonates and in the presence of catalysts to form hexamethylene dialkylurethanes-1,6 and/or isomeric alkylene dialkyl urethanes with 6 carbon atoms in the alkylene residue, while the resulting ammonia is simultaneously removed,
   (b) the alcohol, the dialkyl carbonates, and/or carbamic acid alkyl esters are removed from the resulting reaction mixture and returned to reaction step (a),
   (c) the hexamethylene dialkylurethanes-1,6 and/or isomeric alkylene dialkyl urethanes with 6 carbon atoms in the alkylene residue are evaporated in an evaporator at temperatures from 200° C. to 300° C. and at a pressure of 0.1 mbar to 200 mbar,
   (d) the vaporized diurethanes are thermally cleaved at temperatures of greater than 300° C. and at a pressure of 0.1 to 200 mbar in a cleaving reactor into hexamethylene diisocyanate-1,6, and/or isomeric alkylene diisocyanates with 6 carbon atoms in the alkylene residue, and alcohol, and
   (e) the cleavage products are fractionally condensed.

2. The process of claim 1 wherein the resulting reaction mixture (a) is fractionated in two steps, whereby
   (i) in the first step the alcohol is distilled off until a residual alcohol content of from 1 percent by weight to 30 percent by weight based on the total weight of the residual mixture is reached and said distilled alcohol is returned to reaction step (a) and
   (ii) in the second stage, the remaining alcohol, the dialkyl carbonate, and/or the carbamic acid alkyl ester is removed from the hexamethylene dialkylurethane-1,6 and/or the isomeric alkylene dialkyl urethanes with 6 carbon atoms in the alkylene residue by means of stripping with inert gas and is returned to reaction step (a).

3. The process of claim 2 wherein the remaining alcohol, the dialkyl carbonate, and/or the cabamic acid alkyl ester are separated in a stripping column at temperatures from 50° C. to 200° C. with 50 to 5000 volumes inert gas per volume reaction mixture per hour.

4. The process of claim 1 wherein the products of the cleavage reaction are fractionally condensed in a two-step condensation device, whereby in the first part of the condensation device primarily hexamethylene diisocyanate-1,6 and/or isomeric aliphatic diisocyanates with 6 carbon atoms in the alkylene residue are condensed, and in the second part of the condensation device primarily alcohol is condensed, which along with the residue products obtained in a subsequent purification distillation of the aliphatic diisocyanates is returned to reaction step (a).

5. The process of claim 1 wherein hexamethylenediamine-1,6 and/or isomeric alkylenediamines with 6 carbon atoms in the alkylene residue are reacted with urea and alcohol in a molar ratio of 1 mole diamine to 1.8 to 2.5 moles urea to 2 to 10 moles alcohol in reaction step (a).

6. The process of claim 1 wherein n- and/or isobutanol are used as the alcohols in reaction step (a).

7. The process of claim 1 wherein the carbamic acid alkyl ester corresponding to the alcohol is used in reaction step (a) in amounts from 1 mole percent to 20 mole percent, based on the hexamethylene diamine-1,6 and/or isomeric alkylene diamines with 6 carbon atoms in the alkylene residue.

8. The process of claim 1 wherein the dialkyl carbonate corresponding to the alcohol is used in reaction step (a) in amounts from 1 mole percent to 30 mole percent based on the hexamethylene diamine-1,6 and/or isomeric alkylene diamines with 6 carbon atoms in the alkylene residue.

9. The process of claim 1 wherein the ammonia formed in reaction step (a) is removed from the reaction mixture with the aid of a distillation device at temperatures from 60° C. to 150° C.

10. The process of claim 1 wherein a film evaporator is used as the evaporator and the hexamethylene dialkylurethane-1,6 and/or isomeric alkylene dialkyl urethanes with 6 carbon atoms in the alkylene residue is added in such a manner that from 20 percent by weight to 95 percent by weight hexamethylene dialkylurethane-1,6 and/or isomeric alkylene dialkylurethane-1,6 with 6 carbon atoms in the alkyl residue evaporates and from 5 percent by weight to 80 percent by weight along with any nonvolatile residues present are drained off and returned to reaction step (a).

11. The process of claim 1 wherein the thermal cleavage (d) is performed in the presence of temperature-resistant, gas-permeable packings of steel, brass, copper, zinc, aluminum, titanium, chromium, cobalt, nickel, carbon, and/or quartz in the splitting reactor.

* * * * *